United States Patent [19]

Torii et al.

[11] Patent Number: 4,599,151
[45] Date of Patent: Jul. 8, 1986

[54] PROCESS FOR PREPARING 2,2-BISHALOMETHYLPENAM DERIVATIVES

[75] Inventors: Sigeru Torii; Hideo Tanaka, both of Okayama; Michio Sasaoka, Tokushima; Takashi Shiroi, Tokushima; Seiryu Uto, Tokushima, all of Japan

[73] Assignee: Otsuka Kagaku Kabushiki Kaisha, Osaka, Japan

[21] Appl. No.: 711,922

[22] Filed: Mar. 15, 1985

[30] Foreign Application Priority Data

Mar. 27, 1984 [JP] Japan ............................... 59-60166

[51] Int. Cl.⁴ .......................................... C25B 3/06
[52] U.S. Cl. ................................... 204/59 R; 204/81
[58] Field of Search .................. 204/59 R, 81, 73 R, 204/72

[56] References Cited

U.S. PATENT DOCUMENTS 4,464,237  8/1984  Torii et al. ........................... 204/81
4,482,491 11/1984  Torii et al. ........................... 204/81

OTHER PUBLICATIONS

Heterocycles, vol. 10, 99 (1978), pp. 99–104.

Primary Examiner—R. L. Andrews
Attorney, Agent, or Firm—Armstrong, Nikaido, Marmelstein & Kubovcik

[57] ABSTRACT

This invention provides a process for preparing a 2,2-bishalomethylpenam derivative represented by the formula

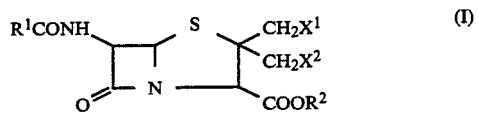

wherein $R^1$ represents a lower alkyl group, aryl group, arylmethyl group, arylcarbonyl group or aryloxymethyl group, $R^2$ represents a carboxyl-protecting group, $X^1$ and $X^2$ are the same or different and represent a halogen atom, the process being characterized in that a disulfide represented by the formula

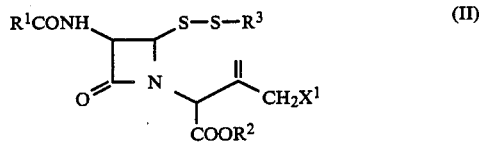

wherein $R^1$, $R^2$ and $X^1$ are as defined above and $R^3$ represents an aryl group or heterocyclic group is subjected to an electrolytic reaction in a solvent in the presence of a halogen acid and/or halogen salt.

10 Claims, No Drawings

PROCESS FOR PREPARING 2,2-BISHALOMETHYLPENAM DERIVATIVES

This invention relates to a process for preparing 2,2-bishalomethylpenam derivatiaves.

2,2-Bishalomethylpenam derivatives obtained by the present process are represented by the formula

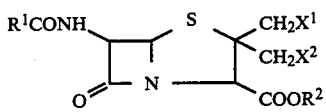

wherein $R^1$ represents a lower alkyl group, aryl group, arylmethyl group, arylcarbonyl group or aryloxymethyl group, $R^2$ represents a carboxyl-protecting group, and $X^1$ and $X^2$ are the same or different and represent each halogen atom.

The 2,2-bishalomethylpenam derivative of the formula (I) can be converted to a cephalosporin compound, for example, according to the process described in J. Org. Chem., 45 (16), 3205 (1980) as shown below, and therefore is an important compound as the intermediate for preparing cephalosporin compounds.

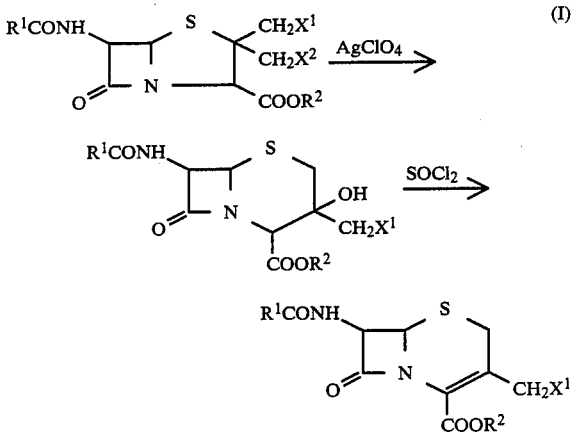

In the foregoing formulas, $R^1$, $R^2$, $X^1$ and $X^2$ are as defined above.

Heretofore, the 2,2-bishalomethylpenam derivatives of the formula (I) have been produced, for example, by reacting bromine with a disulfide of the formula

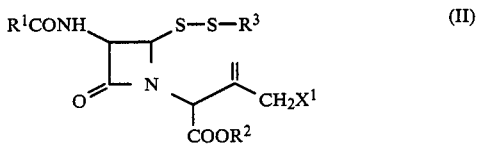

wherein $R^1$, $R^2$ and $X^1$ are as defined above and $R^3$ represents an aryl group or heterocyclic group [Heterocycles, 10, 99 (1978)]. However, the conventional process, when carried out, encounters the disadvantage of requiring bromine which is strongly poisonous and has pungent odor and giving the desired 2,2-bishalomethylpenam derivatives of the formula (I) in fairly high but not fully satisfactory yields, and therefore the conventional process is not highly suitable for industrial use.

An object of the present invention is to provide an industrially advantageous process for preparing the 2,2-bishalomethylpenam derivatives of the formula (I) without the drawbacks of the conventional process.

Another object of the invention is to provide a process for preparing the above 2,2-bishalomethylpenam derivatives without necessitating the use of reactant such as bromine which poses a problem in handling in the conventional process.

Another object of the invention is to provide a process for preparing the above 2,2-bishalomethylpenam derivatives in high yields.

These objects and other features of the invention will become apparent from the following description.

The present invention provides a process for preparing a 2,2-bishalomethylpenam derivative represented by the formula

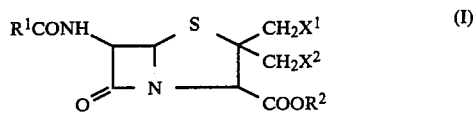

wherein $R^1$ represents a lower alkyl group, aryl group, arylmethyl group, arylcarbonyl group or aryloxymethyl group, $R^2$ represents a carboxyl-protecting group, and $X^1$ and $X^2$ are the same or different and represent a halogen atom, the process being characterized in that a disulfide represented by the formula

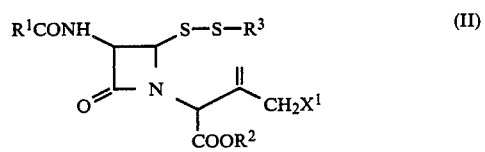

wherein $R^1$, $R^2$ and $X^1$ are as defined above, and $R^3$ represents an aryl group or heterocyclic group is subjectedto an electrolytic reaction in a solvent in the presence of a halogen acid and/or halogen salt which can introduce the halogen atom represented by $X^2$ in the compound of the formula (I).

According to the present process, the desired 2,2-bishalomethylpenam derivative of the formula (I) can be prepared by a simple procedure in high yields. The present process does not necessitate using bromine, and therefore is free from the disadvantages encountered in using bromine. Accordingly, the present process is an extremely advantageous process for industrially preparing 2,2-bishalomethylpenam derivatives (I).

With respect to $R^1$, examples of lower alkyl groups are straight-chain or branched-chain alkyl groups having 1 to 6 carbon atoms, such as methyl, ethyl, isopropyl, butyl, pentyl, hexyl and the like. Examples of the aryl groups are phenyl groups which may be substituted with, for example, nitro, halogen, $C_1$–$C_4$ alkoxy, $C_1$–$C_4$ alkylcarbonyloxy or hydroxy, such as phenyl, p-nitrophenyl, p-chlorophenyl, p-methoxyphenyl, p-acetoxyphenyl, p-hydroxyphenyl, etc.; α-naphthyl amd β-naphthyl; and the like. Examples of arylmethyl groups are those in which methylene or methine group is linked to one or two of the above-mentioned aryl groups, and the methylene group may be substituted with hydroxy group, amino group, $C_1$–$C_{10}$ acylamino group (such as acetylamino, butyrylamino, benzoylamino, etc.), sulfonic acid group or carbamoyl group. Typical examples of the arylmethyl groups are benzyl, p-nitrophenylmethyl, p-chlorophenylmethyl, p-methoxyphenylmethyl, diphenylmethyl, p-acetoxyphenylmethyl, phenylhydroxymethyl, phenylaminomethyl, p-hydroxyphenylaminomethyl, phenyl-(acetylamino)methyl, p-hydroxyphenyl(benzoylamino)methyl, phenylsulfomethyl, phenylcarbamoylmethyl and the like. Examples of arylcarbonyl groups are benzoyl groups which may be substituted with halogen, hydroxy or $C_1$-$C_4$ alkoxy on the phenyl ring, such as benzoyl, p-chlorobenzoyl, p-hydroxybenzoyl, p-methoxybenzoyl and the like. Examples of aryloxymethyl groups are phenoxymethyl groups which may be substituted with halogen, hydroxy or nitro on the phenyl ring, such as phenoxymethyl, p-nitrophenoxymethyl, p-chlorophenoxymethyl, p-bromophenoxymethyl, p-hydroxyphenoxymethyl and the like.

Examples of useful carboxyl-protecting groups represented by $R^2$ are not particularly limited, and any of those mentioned in Chapter 5 of "Protective Groups in Organic Synthesis" by Theodora W. Greene can be used. Typical of useful carboxyl-protecting groups are methyl, ethyl, propyl, tert-butyl, trichloroethyl, methoxymethyl, methoxyethoxymethyl, i-propoxymethyl, 1-methoxycarbonyl-2-oxopropyl, benzyl, o-nitrobenzyl, p-nitrobenzyl, o,p-dinitrobenzyl, p-methoxybenzyl, trimethoxybenzyl, trimethoxydichlorobenzyl, piperonyl, diphenylmethyl, bis(p-methoxyphenyl)methyl, ditolylmethyl, phenyl-p-methoxyphenylmethyl, phenacyl, p-bromophenacyl, benzyloxymethyl, trityl, α-diphenylethyl, α-p-methoxyphenylethyl, α-p-methoxyphenyl-β-trichloroethyl, cumyl, fluorenyl, etc.

With respect to $R^3$, examples of aryl groups are phenyl groups which may be substituted with $C_1$-$C_4$ alkyl, $C_1$-$C_4$ alkoxy, nitro, halogen, etc., such as phenyl, tolyl, xylyl, p-methoxyphenyl, p-nitrophenyl, o-nitrophenyl, 2,4-dinitrophenyl, p-chlorophenyl, p-bromophenyl, p-iodophenyl, pentachlorophenyl and the like. Examples of heterocyclic groups are thiazol-2-yl groups which may be substituted with $C_1$-$C_4$ alkyl or phenyl, such as thiazol-2-yl, 4-methylthiazol-2-yl, 5-methylthiazol-2-yl, 4-phenylthiazol-2-yl, 5-phenylthiazol-2-yl and the like; thiadiazol-2-yl groups which may be substituted with $C_1$-$C_4$ alkyl, phenyl, $C_1$-$C_4$ alkoxy or $C_1$-$C_4$ alkoxycarbonyl, such as thiadiazol-2-yl, 5-methylthiadiazol-2-yl, 5-phenylthiadiazol-2-yl, 5-methoxycarbonylthiadiazol-2-yl, 5-methoxythiadiazol-2-yl and the like; benzothiazol-2-yl groups which may be substituted with $C_1$-$C_4$ alkyl, $C_1$-$C_4$ alkoxy, nitro or halogen, such as benzothiazol-2-yl, 4-methylbenzothiazol-2-yl, 6-methylbenzothiazol-2-yl, 5-methoxybenzothiazol-2-yl, 6-nitrobenzothiazol-2-yl, 5-chlorobenzothiazol-2-yl and the like; benzoxazol-2-yl groups which may be substituted with $C_1$-$C_4$ alkyl, $C_1$-$C_4$ alkoxy, phenyl or halogen, such as benzoxazol-2-yl, 4-methylbenzoxazol-2-yl, 6-phenylbenzoxazol-2-yl, 5-methoxybenzoxazol-2-yl, 5-chlorobenzoxazol-2-yl and the like; benzoimidazol-2-yl groups which may be substituted with $C_1$-$C_4$ alkyl or halogen, such as benzoimidazol-2-yl, 5-methylbenzoimidazol-2-yl, 6-chlorobenzoimidazol-2-yl and the like; pyrimidin-2-yl groups which may be substituted with $C_1$-$C_4$ alkyl, such as pyrimidin-2-yl, 5-methylpyrimidin-2-yl and the like; pyridyl group; etc.

Examples of halogen atoms represented by $X^1$ and $X^2$, or exemplified as the substituent for the above-mentioned groups represented by $R^1$ to $R^3$ are chlorine atom, bromine atom, iodine atom, etc.

The disulfides (II) used as the starting material in the present invention are all known compounds, and can be easily prepared, for example, according to the process described in Japanese unexamined patent publication No. 85894/1983.

The electrolytic reaction in the present invention is usually conducted in a suitable solvent. The solvent is not particularly restricted, but organic solvents are preferred. In the present invention, it is more preferable to use a mixture of water and a organic solvent, because the mixture can dissolve not only disulfide (II) used as the starting material but also the halogen acid and/or halogen salt and because the terminal voltage required to pass the necessary electric current can be lowered. Examples of useful organic solvents are $C_1$-$C_6$ nitriles such as acetonitrile, propionitril, valeronitrile and the like; di($C_2$-$C_6$ alkyl)ethers such as diethyl ether, di-isopropyl ether and the like; cyclic ethers such as tetrahydrofuran, dioxane and the like; $C_1$-$C_4$ halogenated hydrocarbons such as dichloromethane, 1,2-dichloroethane, chloroform, carbon tetrachloride and the like; ketones having $C_1$-$C_4$ alkyls, such as acetone, methyl ethyl ketone, diethyl ketone and the like; esters of $C_1$-$C_6$ fatty acids with $C_1$-$C_6$ aliphatic alchols, such as ethyl formate, ethyl acetate, methyl acetate and the like. Particularly preferable organic solvents are acetonitrile, tetrahydrofuran and dichloromethane. In the present invention, the organic solvents are used singly or in admixture. The amount of water to be admixed with the organic solvent varies with the kind of the organic solvent to be used for the reaction, and can be suitably determined over a wide range. When the organic solvent to be used is a hydrophilic one such as acetonitrile, acetone, dioxane, tetrahydrofuran and the like, the amount of water to be used is preferably about 1 to about 100% by weight, more preferably about 2 to about 10% by weight of the organic solvent. When the organic solvent to be used is a hydrophobic one such as ethyl acetate, dichloromethane, 1,2-dichloroethane, chloroform and the like, the amount of water to be used is preferably about 10 to about 500%, more preferably about 30 to about 70% by weight of the organic solvent.

In the present invention, it is necessary that the halogen acid and/or halogen salt be present in the reaction system. The halogen acid and/or halogen salt can introduce the halogen atom represented by $X^2$. Useful halogen acids are hydrohalogenic acids such as hydrochloric acid, hydrobromic acid and hydriodic acid. Halogen salts useful in the present invention include alkali metal salts or alkaline earth metal salts of the above-mentioned halogen acids. Preferred examples of the halogen salts are $MgCl_2$, $MgBr_2$, $LiCl$, $LiBr$, $KBr$, $NaCl$, $NaBr$, $LiI$, $NaI$, $MgI_2$, $KI$, etc. The amount of the halogen acid and/or the halogen salt to be used is not limited particularly and is suitably variable widely. It is usually at least about 1 mole, preferably about 1.1 to about 1.3 moles per mole of the disulfide (II) used as the starting material.

The electrolytic reaction of the present invention may be carried out in the electrolytic cell which is either not divided or divided into an anode chamber and a cathode chamber. The electrodes to be used are those conventionally used for electrolytic reactions. Examples of the anode materials are platinum, stainless steel, carbon, iron oxide and the like. Titanium surface-treated with platinum, iridium, ruthenium and the like can also be used as the anode material. Examples of the cathode materials are lead, copper, nickel, stainless steel, platinum, carbon, etc.

The electrolysis of the present invention can be performed at either controlled potential or constant current density. However, it is preferable to carry out the electrolysis at constant current density from a viewpoint of simplicity of electrolytic apparatus and ease of operation. The electrolysis is usually carried out at a current density of about 1 to about 500 mA/cm², preferably about 5 to about 50 mA/cm². The amount of electricity to be passed for the present electrolytic reaction is not definite and varies according to the shape of the electrolytic cell, kind of electrodes, kind of disulfides (II) used as the starting material, kind of the organic solvents, reaction temperature, etc. Generally, the amount of electricity is at least 2F (Farad), preferably about 2 to about 20F, per mole of the starting material (II).

The present electrolytic reaction usually can be carried out at a temperature of about −20° to about +50° C., preferably at about −10° to about +30° C.

The desired compound obtained by the process of the present invention can be separated and purified by conventional methods such as column chromatography or the like.

The present invention will be described below in more detail with reference to the following Examples.

EXAMPLE 1

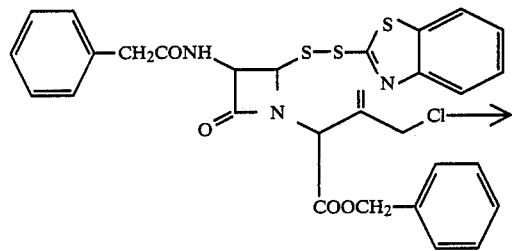

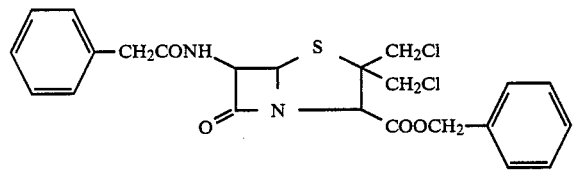

A 65 mg quantity of benzyl 2-[3-phenylacetamido-4-(2-benzothiazolyldithio)-2-azetidinon-1-yl]-3-chloromethyl-3-butenoate was dissolved in a solvent mixture of 6 ml of acetonitrile and 1.5 ml of tetrahydrofuran. To the solution was added a solution of 4.7 mg of MgCl₂.6H₂O in 0.3 ml of H₂O to prepare an electrolytic solution. The solution was subjected to electrolysis in a cell equipped with two platinum plates each having a surface area of 3 cm² as anode and cathode under the conditions of a constant current density of 10 mA/cm², a terminal voltage of 11 to 18 V and a reaction temperature of 24° to 29° C. After applying 8.25 F of electricity permole of the benzyl 2-[3-phenylacetamido-4-(2-benzothiazolyldithio)-2-azetidinon-1-yl]-3-chloromethyl-3-butenoate, the electrolytic solution was concentrated in a vacuum to about 2 ml, and 10 ml of chloroform and 0.5 ml of water were added to the concentrate for extraction. Subsequently the chloroform layer was separated and dried on anhydrous sodium sulfate, and then concentrated in a vacuum. The resulting concentrate was subjected to silica gel column chromatography (eluent: benzene-ethyl acetate, V/V=9:1), affording 45.7 mg of benzyl 6-phenylacetamido-2,2-dichloromethylpenam-3-carboxylate. Yield 89%.

IR spectrum (CHCl₃): 3380, 1790, 1745, 1675, 1500 cm⁻¹.

NMR spectrum (CDCl₃, δ, ppm): 3.37 and 3.70 (2H, ABq, J=12 Hz), 3.60 (2H, s), 3.50 and 3.95 (2H, ABq, J=11 Hz), 4.91 (1H, s), 5.16 (2H, s), 5.4–5.7 (2H, m), 6.29 (1H, br. d, J=8 Hz), 7.2–7.4 (10H, m).

EXAMPLE 2

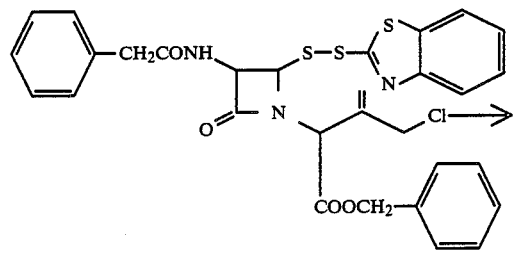

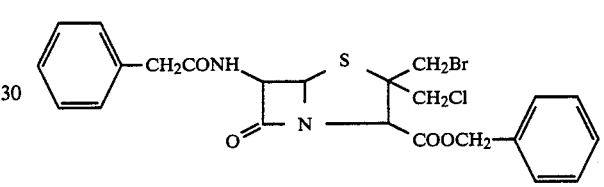

A 220 mg quantity of benzyl 2-[3-phenylacetamido-4-(2-benzothiazolyldithio)-2-azetidinon-1-yl]-3-chloromethyl-3-butenoate was dissolved in a solvent mixture of 13.2 ml of acetonitrile and 3.3 ml of tetrahydrofuran. To the solution was added a solution of 118 mg of MgBr₂.6H₂O in 0.66 ml of water to prepare an electrolytic solution. The solution was subjected to electrolysis in the same manner as in Example 1 except that the terminal voltage was changed to 10 to 14 V and the amount of electricity was changed to 7.93 F/mol. The electrolysis gave 174.5 mg of benzyl 6-phenylacetamido-2-bromomethyl-2-chloromethylpenam-3-carboxylate in a yield of 92%.

IR spectrum (CHCl₃): 3385, 1785, 1745, 1675, 1494 cm⁻¹.

NMR spectrum (CDCl₃, δ, ppm): 3.39 and 3.73 (2H, ABq, J=12 Hz), 3.56 (2H, s), 3.48 and 3.95 (2H, ABq, J=11 Hz), 4.91 (1H, s), 5.13 (2H, s), 5.3–5.6(2H, m), 6.57 (1H, br. d, J=8 Hz), 7.2–7.4 (10H, m).

EXAMPLES 3-5

The general procedure of Example 1 was followed under the conditions as shown below in Table 1 with use of methyl 2-[3-phenylacetamido-4-(2-benzothiazolyldithio)-2-azethidinon-1-yl]-3-chloromethyl-3-butenoate as starting material. The spectral data of the resulting products are shown below in Table 2. The same products were obtained in Example 3 and Example 4.

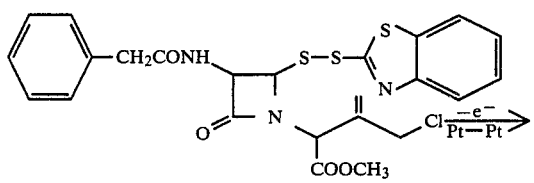

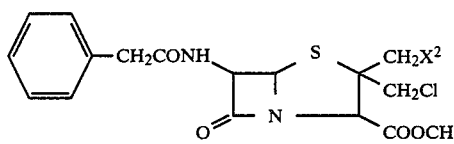

TABLE 1

| Ex. | Halogen salt | Amount of electricity* (F/mol) | Solvent (ml) | Product X² | Yield (%) |
|---|---|---|---|---|---|
| 3 | MgBr₂ | 4 | CH₃CN—THF—H₂O (2.4/0.6/0.12) | Br | 85 |
| 4 | NaBr | 4 | CH₃CN—THF—H₂O (2.4/0.6/0.12) | Br | 90 |
| 5 | NaCl | 6 | CH₂Cl₂—H₂O (2/1) | Cl | 94 |

*Amount of electricity per mole of the starting material

TABLE 2

| Ex. | IR spectrum (neat) cm⁻¹ | NMR spectrum (CDCl₃, δ, ppm) |
|---|---|---|
| 3 | 3290 | 3.30 and 3.66 (2H, ABq, J = 11.2 Hz), |
| 4 | 1779 | 3.65 (2H, s), 3.80 (3H, s), |
|  | 1743 | 3.70 and 4.14 (2H, ABq, J = 11.2 Hz), |
|  | 1665 | 4.98 (1H, s), 5.5–5.7 (2H, m), |
|  |  | 6.20 (1H, br. d, J = 8 Hz), 7.35 (5H, m) |
| 5 | 3420 | 3.43 and 3.76 (2H, ABq, J = 12.5 Hz), |
|  | 1785 | 3.65 (2H, s), 3.80 (3H, s), |
|  | 1748 | 3.70 and 4.10 (2H, ABq, J = 13.0 Hz), |
|  | 1673 | 4.94 (1H, s), 5.4–5.7 (2H, m), |
|  |  | 6.30 (1H, br. d, J = 8 Hz), 7.30 (5H, m) |

EXAMPLES 6 TO 8

Following the general procedure of Example 1 and using the halogen acid and/or halogen salt listed in Table 3, the compounds of the invention were prepared. Example 6 and 7 gave the same product as that of Example 1, whereas Example 8 afforded a corresponding iodo-derivative, i.e., benzyl 6-phenylacetamido-2-chloromethyl-2-iodomethylpenam-3-carboxylate. Table 3 also shows the yields of the products obtained, and Table 4 below shows the spectral data of the product of Example 8.

TABLE 3

| Example | Halogen acid and/or halogen salt | Yield (%) |
|---|---|---|
| 6 | 5% hydrochloric acid (0.2 ml) | 90 |
| 7 | MgCl₂.6H₂O (2.3 mg) + 1% hydrochloric acid (0.4 ml) | 91 |
| 8 | NaI (2.6 mg) | 87 |

TABLE 4

| IR spectrum (neat) cm⁻¹ | NMR spectrum (CDCl₃, δ, ppm) |
|---|---|
| 3380 | 3.40 and 3.75 (2H, ABq, J = 12 Hz), |
| 1785 | 3.58 (2H, s), |
| 1750 | 3.46 and 3.95 (2H, ABq, J = 11 Hz), |
| 1675 | 4.91 (1H, s), 5.15 (2H, s), |

TABLE 4-continued

| IR spectrum (neat) cm⁻¹ | NMR spectrum (CDCl₃, δ, ppm) |
|---|---|
| 1495 | 5.2–5.5 (2H, m), 6.60 (1H, br. d, J = 8 Hz), 7.2–7.4 (10H, m) |

EXAMPLES 9 TO 13

The procedure of Example 1 was repeated with the exception of using the electrodes listed in Table 5, giving the same product as that of Example 1. Table 5 also shows the yields of the product thus prepared.

TABLE 5

| Example | Anode | Cathode | Yield (%) |
|---|---|---|---|
| 9 | C | Pt | 87 |
| 10 | Pt | Stainless steel | 93 |
| 11 | Ti coated with Pt | Cu | 88 |
| 12 | Stainless steel | Ni | 85 |
| 13 | iron oxide | C | 87 |

EXAMPLES 14 TO 16

The procedure of Example 1 was repeated with the exception of using the disulfide of the formula

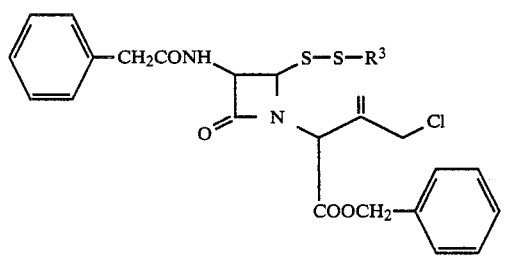

wherein R³ is as shown in Table 6 below. The reaction gave the same product as that of Example 1. The yields are shown in Table 6.

TABLE 6

| Example | R³ | Yield (%) |
|---|---|---|
| 14 | ![pentachlorophenyl] | 89 |
| 15 | ![5-methyl-1,3,4-thiadiazol-2-yl] | 87 |
| 16 | ![6-methoxybenzothiazol-2-yl] | 90 |

We claim:

1. A process for preparing a 2,2-bishalomethylpenam derivative represented by the formula

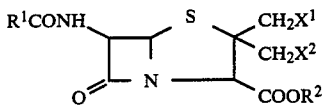

(I)

wherein $R^1$ represents a lower alkyl group, aryl group, arylmethyl group, arylcarbonyl group or aryloxymethyl group, $R^2$ represents a carboxyl-protecting group, $X^1$ and $X^2$ are the same or different and represent a halogen atom, the process being characterized in that a disulfide represented by the formula

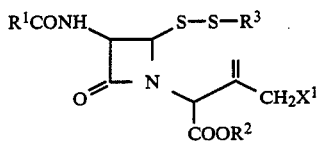

(II)

wherein $R^1$, $R^2$ and $X^1$ are as defined above and $R^3$ represents an aryl group or heterocyclic group is subjected to an electrolytic reaction in a solvent in the presence of a halogen acid and/or halogen salt.

2. A process as defined in claim 1 wherein $R^1$ is $C_1$-$C_6$ alkyl group; phenyl group which may be substituted with nitro, halogen, $C_1$-$C_4$ alkoxy, $C_1$-$C_4$ alkylcarbonyloxy or hydroxy; α- or β-naphthyl; phenylmethyl group which may be substituted with nitro, halogen $C_1$-$C_4$ alkoxy, $C_1$-$C_4$ alkylcarbonyloxy or hydroxy on the phenyl ring and which may be substituted with hydroxy, amino, $C_1$-$C_{10}$ acylamino, sulfo or carbamoyl on the methylene group; diphenylmethyl; α- or β-naphthylmethyl group; benzoyl group which may be substituted with halogen, hydroxy or $C_1$-$C_4$ alkoxy on the phenyl ring; or phenoxymethyl group which may be substituted with halogen, hydroxy or nitro on the phenyl ring.

3. A process as defined in claim 1 wherein $R^3$ is a phenyl group which may be substituted with $C_1$-$C_4$ alkyl, $C_1$-$C_4$ alkoxy, nitro or halogen; thiazol-2-yl group which may be substituted with $C_1$-$C_4$ alkyl or phenyl; thiadiazol-2-yl group which may be substituted with $C_1$-$C_4$ alkyl, phenyl, $C_1$-$C_4$ alkoxy or $C_1$-$C_4$ alkoxycarbonyl; benzothiazol-2-yl group which may be substituted with $C_1$-$C_4$ alkyl, $C_1$-$C_4$ alkoxy, nitro or halogen; benzoxazol-2-yl group which may be substituted with $C_1$-$C_4$ alkyl, $C_1$-$C_4$ alkoxy, phenyl or halogen; benzoimidazol-2-yl group which may be substituted with $C_1$-$C_4$ alkyl or halogen; pyrimidin-2-yl group which may be substituted with $C_1$-$C_4$ alkyl; or pyridyl group.

4. A process as defined in claim 1 wherein $X^1$ and $X^2$ are the same or different and are chlorine atom, bromine atom or iodine atom.

5. A process as defined in claim 1 wherein pg,22 the halogen acid is hydrochloric acid, hydrobromic acid or hydriodic acid.

6. A process as defined in claim 1 wherein the halogen salt is alkali metal salt or alkaline earth metal salt of the halogen acid.

7. A process as defined in claim 6 wherein the halogen salt is LiCl, LiBr, NaCl, NaBr, KBr, $MgCl_2$, $MgBr_2$, LiI, NaI, $MgI_2$ or KI.

8. A process as defined in claim 1 wherein the solvent is an organic solvent.

9. A process as defined in claim 1 wherein the solvent is a mixture of water and an organic solvent.

10. A process as defined in claim 1 wherein the electrolytic reaction is conducted by passing at least 2 F of electricity per mole of the compound of the formula (II).

* * * * *